US012251268B2

(12) United States Patent
Shin et al.

(10) Patent No.: US 12,251,268 B2
(45) Date of Patent: Mar. 18, 2025

(54) GRATING LOBES REDUCTION FOR ULTRASOUND IMAGES AND ASSOCIATED DEVICES, SYSTEMS, AND METHODS

(71) Applicant: KONINKLIJKE PHILIPS N.V., Eindhoven (NL)

(72) Inventors: Jun Seob Shin, Medford, MA (US); Seungsoo Kim, Andover, MA (US); Francois Guy Gerard Marie Vignon, Andover, MA (US); David Hope Simpson, Bothell, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/867,997

(22) Filed: Jul. 19, 2022

(65) Prior Publication Data
US 2022/0354465 A1 Nov. 10, 2022

Related U.S. Application Data

(63) Continuation of application No. 16/560,727, filed on Sep. 4, 2019, now Pat. No. 11,389,138.
(Continued)

(51) Int. Cl.
*A61B 8/00* (2006.01)
*A61B 8/14* (2006.01)
(Continued)

(52) U.S. Cl.
CPC .............. *A61B 8/5207* (2013.01); *A61B 8/14* (2013.01); *A61B 8/4488* (2013.01);
(Continued)

(58) Field of Classification Search
CPC ....... A61B 8/5207; A61B 8/14; A61B 8/4488; A61B 8/5269; A61B 8/06; A61B 8/0891;
(Continued)

(56) References Cited

U.S. PATENT DOCUMENTS 5,974,098 A 10/1999 Tsuda
6,014,897 A 1/2000 Mo
(Continued)

FOREIGN PATENT DOCUMENTS

JP 11000328 A 1/1999
WO 2019057461 A1 3/2019

OTHER PUBLICATIONS

Dantas, Ricardo G. et al "Ultrasound Speckle Reduction using Modified Gabor Filters", IEEE Transactions on Ultrasonics, Ferroelectrics, and Frequency Control, vol. 54, No. 3. Mar. 2007.
(Continued)

*Primary Examiner* — Pascal M Bui Pho
*Assistant Examiner* — Taylor Deutsch

(57) ABSTRACT

Improved ultrasound imaging devices and methods of operating the devices that minimize grating lobe artifacts in an ultrasound image are provided. For example, an ultrasound imaging system analyzes the ultrasound data at different frequency bands and generates a grating-lobe-minimized image based on minimum signals identified for each pixel among the plurality of frequency ranges. In one embodiment, an ultrasound imaging system includes an ultrasound transducer array configured to obtain ultrasound data, and a processor in communication with the ultrasound transducer array. The processor is configured to receive the ultrasound data, generate an ultrasound image based on a first frequency range of the ultrasound data, generate a grating-lobe-minimized ultrasound image based on a plurality of second frequency ranges of the ultrasound data, combine the ultrasound image and the grating-lobe-minimized ultrasound image to generate a combined ultrasound image, and output the combined ultrasound image to a display.

13 Claims, 12 Drawing Sheets

Related U.S. Application Data

(60) Provisional application No. 62/729,078, filed on Sep. 10, 2018.

(51) Int. Cl.
| | | |
|---|---|---|
| *G01S 7/00* | (2006.01) | |
| *G01S 7/52* | (2006.01) | |
| *A61B 8/06* | (2006.01) | |
| *A61B 8/08* | (2006.01) | |
| *A61B 8/12* | (2006.01) | |
| *G01S 15/89* | (2006.01) | |

(52) U.S. Cl.
CPC ........ *A61B 8/5269* (2013.01); *G01S 7/52047* (2013.01); *A61B 8/06* (2013.01); *A61B 8/0891* (2013.01); *A61B 8/12* (2013.01); *A61B 8/4444* (2013.01); *G01S 7/5208* (2013.01); *G01S 15/8952* (2013.01)

(58) Field of Classification Search
CPC ......... A61B 8/12; A61B 8/4444; A61B 8/445; G01S 7/52047; G01S 7/5208; G01S 15/8952; G01S 7/52026; G01S 7/52077; G01S 15/8915; G01S 15/892
See application file for complete search history.

(56) References Cited

U.S. PATENT DOCUMENTS

| | | | |
|---|---|---|---|
| 6,162,174 A * | 12/2000 | Friemel | G01S 7/52026 600/447 |
| 6,251,074 B1 | 6/2001 | Averkiou | |
| 6,776,763 B2 | 8/2004 | Nix | |
| 7,226,417 B1 | 6/2007 | Eberle | |
| 7,846,101 B2 | 12/2010 | Eberle | |
| 2005/0033165 A1 | 2/2005 | Ustuner | |
| 2005/0101865 A1 | 5/2005 | Hao | |
| 2009/0129651 A1 * | 5/2009 | Zagzebski | G01S 7/52046 382/131 |
| 2009/0141957 A1 * | 6/2009 | Yen | G01S 15/8977 600/437 |
| 2009/0275812 A1 | 11/2009 | Reichgott | |
| 2011/0087104 A1 * | 4/2011 | Moore | G01S 7/52071 600/447 |
| 2011/0118604 A1 | 5/2011 | Kim | |
| 2011/0245669 A1 | 10/2011 | Zhang | |
| 2014/0180105 A1 * | 6/2014 | Hancock | A61B 8/467 600/443 |
| 2015/0305710 A1 | 10/2015 | Stigall | |
| 2017/0103498 A1 | 4/2017 | Waters | |

OTHER PUBLICATIONS

Ponnle, Akinlolu et al "Suppression of Grating Lobe Artifacts in Ultrasound Images formed from Diverging Transmitting Beams by Modulation of receiving Beams", Ultrasound in Medicine and Biology, vol. 39, No. 4, Apr. 2013, pp. 681-691.

Ponnle, Akinlolu et al "Multi Element Diverging Beam from a Linear Array Transducer for Transverse cross Sectional Imaging of carotid Artery: Simulations and Phantom Vessel validation", Japanese Journal of Applied Physics, vol. 50, 2011.

* cited by examiner

GRATING LOBES REDUCTION FOR ULTRASOUND IMAGES AND ASSOCIATED DEVICES, SYSTEMS, AND METHODS

CROSS-REFERENCE TO RELATED APPLICATIONS

The application is a continuation of U.S. application Ser. No. 16/560,727, filed Sep. 4, 2019, now U.S. Pat. No. 11,389,138, which claims the benefit of and priority to U.S. Provisional Application No. 62/729,078, filed Sep. 10, 2018, the entirety of each of which is incorporated by reference herein.

TECHNICAL FIELD

The present disclosure relates generally to medical imaging and, in particular, to ultrasonic medical imaging devices configured to generate grating-lobe-minimized ultrasound image. For example, an ultrasonic medical imaging device can include an array of acoustic elements configured to obtain ultrasound data, the array being in communication with a processor configured to process the obtained ultrasound data at a plurality of different frequency ranges.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

Solid-state (also known as synthetic-aperture) IVUS catheters are one of the two types of IVUS devices commonly used today, the other type being the rotational IVUS catheter. Solid-state IVUS catheters carry a scanner assembly that includes an array of ultrasound transducers distributed around its circumference along with one or more integrated circuit controller chips mounted adjacent to the transducer array. The controllers select individual acoustic elements (or groups of elements) for transmitting an ultrasound pulse and for receiving the ultrasound echo signal. By stepping through a sequence of transmit-receive pairs, the solid-state IVUS system can synthesize the effect of a mechanically scanned ultrasound transducer but without moving parts (hence the solid-state designation). Since there is no rotating mechanical element, the transducer array can be placed in direct contact with the blood and vessel tissue with minimal risk of vessel trauma. Furthermore, because there is no rotating element, the electrical interface is simplified. The solid-state scanner can be wired directly to the imaging system with a simple electrical cable and a standard detachable electrical connector, rather than the complex rotating electrical interface required for a rotational IVUS device.

In IVUS imaging, a common clinical goal is reducing ultrasound image artifacts, such as grating lobes. Grating lobes, which appear as blurry, off-axis duplicates of on-axis objects, can arise in ultrasound images when the field of view is spatially undersampled. Spatially undersampled arrays do not satisfy the Nyquist sampling criterion, which requires that the pitch, or spacing between acoustic elements in the array, be smaller than half the center wavelength. Given the frequencies at which IVUS imaging devices operate, it may be difficult to manufacture IVUS imaging arrays with acoustic elements and spacing that satisfy the Nyquist criterion.

SUMMARY

Embodiments of the present disclosure provide improved ultrasound imaging devices and methods of operating the devices that minimize grating lobe artifacts in an ultrasound image. For example, an ultrasound imaging device can include an array of acoustic elements configured to emit ultrasound energy and receive echoes corresponding to the emitted ultrasound energy. A processor analyzes the ultrasound data at a plurality of frequency ranges or bands and generates a grating-lobe-minimized image based on minimum signals identified for each pixel among the plurality of frequency ranges. The grating-lobe-minimized image can be output to a display or combined with the original ultrasound image to include image features lost or reduced in the grating-lobe-minimized image. The grating-lobe-minimized image advantageously reduces image artifacts and clutter to simplify ultrasound image analysis and diagnosis procedures.

According to one embodiment, an ultrasound imaging system includes an ultrasound transducer array comprising a plurality of acoustic elements configured to emit ultrasound energy and receive echoes corresponding to the emitted ultrasound energy, and a processor in communication with the ultrasound transducer array. The processor is configured to receive, from the ultrasound transducer array, ultrasound data representative of the received echoes, generate an ultrasound image based on a first frequency range of the ultrasound data, generate a grating-lobe-minimized ultrasound image based on a plurality of second frequency ranges of the ultrasound data, combine the ultrasound image and the grating-lobe-minimized ultrasound image to generate a combined ultrasound image, and output the combined ultrasound image to a display. The first frequency range is broader than each of the plurality of second frequency ranges.

In some embodiments the ultrasound imaging system further comprises an intravascular ultrasound (IVUS) imaging catheter, wherein the ultrasound transducer array is positioned around a circumference of the IVUS imaging catheter. In some embodiments, the processor is configured to generate the grating-lobe-minimized ultrasound image by duplicating the ultrasound data into a plurality of duplicate ultrasound data sets and applying a different band-pass filter to each of the duplicate ultrasound data sets. The different band-pass filters corresponding to the plurality of second frequency ranges. In one aspect, the processor is configured to generate duplicate ultrasound images from the duplicate ultrasound data sets. Generating the duplicate ultrasound images can include normalizing each of the duplicate ultrasound data sets. In still other embodiments, the ultrasound data is representative of a field of view that includes an anatomy, and the processor is configured to generate the grating-lobe-minimized ultrasound image by analyzing the ultrasound data at the plurality of second frequency ranges to identify a plurality of minimum signals. The plurality of minimum signals can respectively correspond to a plurality of locations within the field of view.

In still other aspects, the processor is configured to combine the ultrasound image with the grating-lobe-minimized ultrasound image by applying a first spatial low-pass filter (LPF) to the grating-lobe-minimized ultrasound image to generate an LPF grating-lobe-minimized ultrasound image, applying a second spatial LPF to the ultrasound image to generate an LPF ultrasound image, subtracting the LPF ultrasound image from the ultrasound image to generate a high spatial frequency ultrasound image, and adding the LPF grating-lobe-minimized ultrasound image and the high spatial frequency ultrasound image. The system of claim 1, wherein the processor is configured to: generate the ultrasound image by applying, to the ultrasound data, a wide band-pass filter corresponding to the first frequency range; and generate the grating-lobe-minimized ultrasound image by applying, to the ultrasound data, a plurality of narrow band-pass filters corresponding to the plurality of second frequency ranges. The system of claim 8, wherein the wide band-pass filter is centered at a center frequency and comprises a bandwidth of about 50%, and wherein each of the plurality of second frequency ranges comprises a bandwidth of about 20%.

In another embodiment, a method for ultrasound imaging includes receiving, by a processor, ultrasound data obtained by an ultrasound transducer array comprising a plurality of acoustic elements, generating, by the processor, an ultrasound image based on a first frequency range of the ultrasound data, generating, by the processor, a grating-lobe-minimized ultrasound image based on a plurality of second frequency ranges of the ultrasound data, wherein the first frequency range is broader than each of the plurality of second frequency ranges, combining, by the processor, the ultrasound image and the grating-lobe-minimized ultrasound image to generate a combined ultrasound image, and outputting, by the processor, the combined ultrasound image to a display.

In some aspects, receiving the ultrasound data comprises receiving the ultrasound data obtained by an intravascular ultrasound (IVUS) imaging catheter, wherein the ultrasound transducer array is positioned around a circumference of the IVUS imaging catheter. In other embodiments, generating the grating-lobe-minimized ultrasound image comprises duplicating the ultrasound data into a plurality of duplicate ultrasound data sets and applying a different band-pass filter to each of the duplicate ultrasound data sets. The different band-pass filters can correspond to the plurality of second frequency ranges. In some embodiments, the method further includes generating duplicate ultrasound images from the duplicate ultrasound data sets. Generating the duplicate ultrasound images can include normalizing each of the duplicate ultrasound data sets. In still other embodiments, the ultrasound data is representative of a field of view that includes an anatomy and generating the grating-lobe-minimized ultrasound image comprises analyzing the ultrasound data at each frequency range of the plurality of second frequency ranges to identify a plurality of minimum signals, wherein each of the plurality of minimum signals corresponds to a different location within the field of view.

In some embodiments, combining the ultrasound image with the grating-lobe-minimized ultrasound image comprises applying a first spatial low-pass filter (LPF) to the grating-lobe-minimized ultrasound image to generate an LPF grating-lobe-minimized ultrasound image, applying a second spatial LPF to the ultrasound image to generate an LPF ultrasound image, subtracting the LPF ultrasound image from the ultrasound image to generate a high spatial frequency ultrasound image, and adding the LPF grating-lobe-minimized ultrasound image and the high spatial frequency ultrasound image. In one aspect, generating the ultrasound image comprises applying, to the ultrasound data, a wide band-pass filter corresponding to the first frequency range. Generating the grating-lobe-minimized ultrasound image can include applying, to the ultrasound data, a plurality of narrow band-pass filters corresponding to the plurality of second frequency ranges. In still other aspects, the wide band-pass filter is centered at a center frequency and comprises a bandwidth of about 50%, and each of the plurality of second frequency ranges comprises a bandwidth of about 20%.

According to another embodiment, an ultrasound imaging system includes an ultrasound transducer array comprising a plurality of acoustic elements configured to emit ultrasound energy and receive echoes associated with the emitted ultrasound energy, and a processor in communication with the array. The processor is configured to receive, from the ultrasound transducer array, ultrasound data representative of the received echoes in a field of view, apply a plurality of different band-pass filters to the ultrasound data to generate a plurality of ultrasound images, analyze the plurality of ultrasound images to identify a plurality of minimum signals, each of the plurality of minimum signals corresponding to a different location in the field of view, and generate a grating-lobe-minimized ultrasound image by selecting a minimum signal corresponding to each of a plurality of locations of the field of view, wherein each minimum signal is selected from a corresponding location in one of the plurality of ultrasound images.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
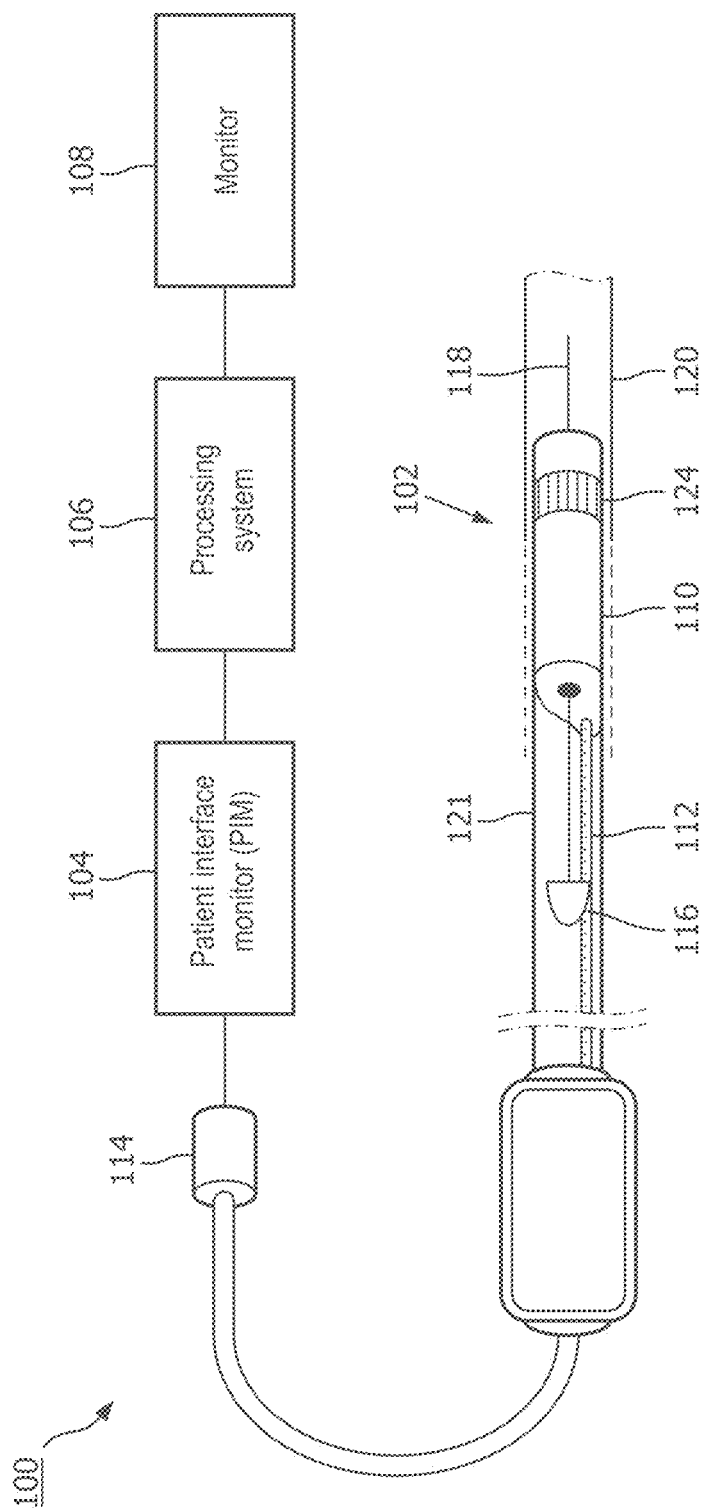
FIG. 1 is a diagrammatic schematic view of an intraluminal imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an ultrasound imaging system 100, according to aspects of the present disclosure. The ultrasound imaging system 100 can be an intraluminal imaging system. In some instances, the system 100 can be an intravascular ultrasound (IVUS) imaging system. The system 100 may include an intraluminal imaging device 102 such as a catheter, guide wire, or guide catheter, a patient interface module (PIM) 104, a processing system or console 106, and a monitor 108. The intraluminal imaging device 102 can be an ultrasound imaging device. In some instances, the device 102 can be IVUS imaging device, such as a solid-state IVUS device.

At a high level, the IVUS device 102 emits ultrasonic energy, or ultrasound signals, from a transducer array 124 included in scanner assembly 110 mounted near a distal end of the catheter device. The ultrasonic energy is reflected by tissue structures in the medium, such as a vessel 120, or another body lumen surrounding the scanner assembly 110, and the ultrasound echo signals are received by the transducer array 124. In that regard, the device 102 can be sized, shaped, or otherwise configured to be positioned within the body lumen of a patient. The PIM 104 transfers the received echo signals to the console or computer 106 where the ultrasound image (including the flow information) is reconstructed and displayed on the monitor 108. The console or computer 106 can include a processor and a memory. The computer or computing device 106 can be operable to facilitate the features of the IVUS imaging system 100 described herein. For example, the processor can execute computer readable instructions stored on the non-transitory tangible computer readable medium.

The PIM 104 facilitates communication of signals between the IVUS console 106 and the scanner assembly 110 included in the IVUS device 102. This communication includes the steps of: (1) providing commands to integrated circuit controller chip(s) 206A, 206B, illustrated in FIG. 2, included in the scanner assembly 110 to select the particular transducer array element(s), or acoustic element(s), to be used for transmit and receive, (2) providing the transmit trigger signals to the integrated circuit controller chip(s) 206A, 206B included in the scanner assembly 110 to activate the transmitter circuitry to generate an electrical pulse to excite the selected transducer array element(s), and/or (3) accepting amplified echo signals received from the selected transducer array element(s) via amplifiers included on the integrated circuit controller chip(s) 206A, 206B of the scanner assembly 110. In some embodiments, the PIM 104 performs preliminary processing of the echo data prior to relaying the data to the console 106. In examples of such embodiments, the PIM 104 performs amplification, filtering, and/or aggregating of the data. In an embodiment, the PIM 104 also supplies high- and low-voltage DC power to support operation of the device 102 including circuitry within the scanner assembly 110.

The IVUS console 106 receives the echo data from the scanner assembly 110 by way of the PIM 104 and processes the data to reconstruct an image of the tissue structures in the medium surrounding the scanner assembly 110. The console 106 outputs image data such that an image of the vessel 120, such as a cross-sectional image of the vessel 120, is displayed on the monitor 108. Vessel 120 may represent fluid filled or surrounded structures, both natural and man-made. The vessel 120 may be within a body of a patient. The vessel 120 may be a blood vessel, as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be used to examine man-made structures such as, but without limitation, heart valves, stents, shunts, filters and other devices.

Figure 2:
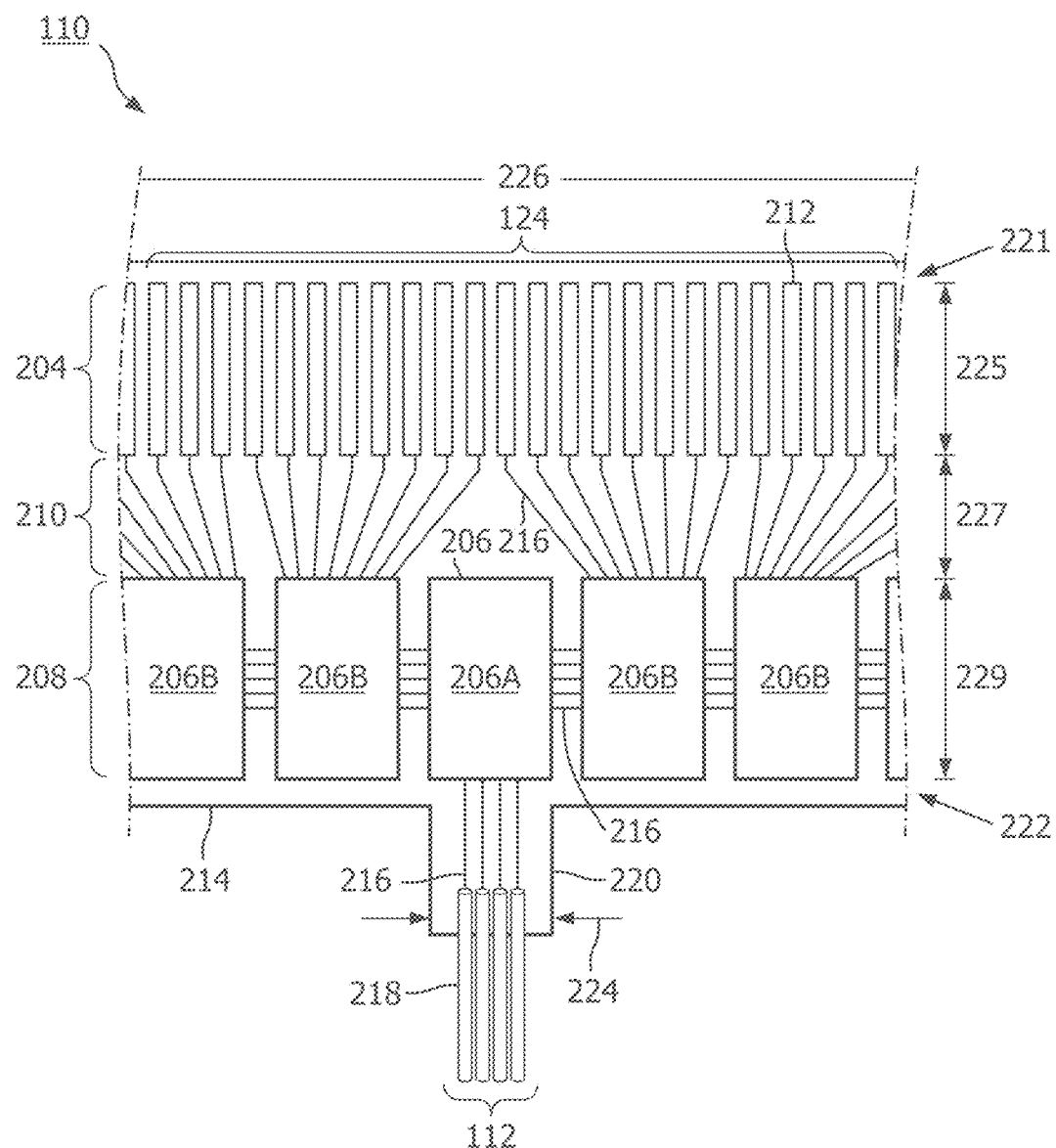
FIG. 2 is a diagrammatic perspective view of the top of a scanner assembly in a flat configuration, according to aspects of the present disclosure.

In some embodiments, the IVUS device includes some features similar to traditional solid-state IVUS catheters, such as the EagleEye® catheter available from Volcano Corporation and those disclosed in U.S. Pat. No. 7,846,101 hereby incorporated by reference in its entirety. For example, the IVUS device 102 includes the scanner assembly 110 near a distal end of the device 102 and a transmission line bundle 112 extending along the longitudinal body of the device 102. The transmission line bundle or cable 112 can include a plurality of conductors, including one, two, three, four, five, six, seven, or more conductors 218 (FIG. 2). It is understood that any suitable gauge wire can be used for the conductors 218. In an embodiment, the cable 112 can include a four-conductor transmission line arrangement with, e.g., 41 AWG gauge wires. In an embodiment, the cable 112 can include a seven-conductor transmission line arrangement utilizing, e.g., 44 AWG gauge wires. In some embodiments, 43 AWG gauge wires can be used.

The transmission line bundle 112 terminates in a PIM connector 114 at a proximal end of the device 102. The PIM connector 114 electrically couples the transmission line bundle 112 to the PIM 104 and physically couples the IVUS device 102 to the PIM 104. In an embodiment, the IVUS device 102 further includes a guide wire exit port 116. Accordingly, in some instances the IVUS device is a rapid-exchange catheter. The guide wire exit port 116 allows a guide wire 118 to be inserted towards the distal end in order to direct the device 102 through the vessel 120.

In an embodiment, the image processing system 106 generates flow data by processing the echo signals from the IVUS device 102 into Doppler power or velocity information. The image processing system 106 may also generate B-mode data by applying envelope detection and logarithmic compression on the conditioned echo signals. The processing system 106 can further generate images in various views, such as 2D and/or 3D views, based on the flow data or the B-mode data. The processing system 106 can also perform various analyses and/or assessments. For example, the processing system 106 can apply virtual histology (VH) techniques, for example, to analyze or assess plaques within a vessel (e.g., the vessel 120). The images can be generated to display a reconstructed color-coded tissue map of plaque composition superimposed on a cross-sectional view of the vessel.

In an embodiment, the processing system 106 can apply a blood flow detection algorithm (e.g., ChromaFlo™) to determine the movement of blood flow, for example, by acquiring image data of a target region (e.g., the vessel 120) repeatedly and determining the movement of the blood flow from the image data. The blood flow detection algorithm operates based on the principle that signals measured from vascular tissue are relatively static from acquisition to acquisition, whereas signals measured from blood flow vary at a characteristic rate corresponding to the flow rate. As such, the blood flow detection algorithm may determine movements of blood flow based on variations in signals measured from the target region between repeated acquisitions. To acquire the image data repeatedly, the processing system 106 may control to the device 102 to transmit repeated pulses on the same aperture.

While the present disclosure refers to intravascular ultrasound (IVUS) imaging using an intravascular catheter or guidewire, it is understood that one or more aspects of the present disclosure can be implemented in any suitable ultrasound imaging system, including a synthetic aperture ultrasound imaging system, a phased array ultrasound imaging system, or any other array-based ultrasound imaging system. For example, aspects of the present disclosure can be implemented in intraluminal ultrasound imaging systems using an intracardiac (ICE) echocardiography catheter and/or a transesophageal echocardiography (TEE) probe, and/or external ultrasound imaging system using an ultrasound probe configured for imaging while positioned adjacent to and/or in contact with the patient's skin. The ultrasound imaging device can be a transthoracic echocardiography (TTE) imaging device in some embodiments.

An ultrasound transducer array of ultrasound imaging device includes an array of acoustic elements configured to emit ultrasound energy and receive echoes corresponding to the emitted ultrasound energy. In some instances, the array may include any number of ultrasound transducer elements. For example, the array can include between 1 acoustic element and 1000 acoustic elements, including values such as 2 acoustic elements, 4 acoustic elements, acoustic elements, 64 acoustic elements, 128 acoustic elements, 500 acoustic elements, 812 acoustic elements, and/or other values both larger and smaller. In some instances, the transducer elements of the array may be arranged in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of transducer elements (e.g., one or more rows, one or more columns, and/or one or more orientations) can be uniformly or independently controlled and activated. The array can be configured to obtain one-dimensional, two-dimensional, and/or three-dimensional images of patient anatomy.

The ultrasound transducer elements may comprise piezoelectric/piezoresistive elements, piezoelectric micromachined ultrasound transducer (PMUT) elements, capacitive micromachined ultrasound transducer (CMUT) elements, and/or any other suitable type of ultrasound transducer elements. The ultrasound transducer elements of the array are in communication with (e.g., electrically coupled to) electronic circuitry. For example, the electronic circuitry can include one or more transducer control logic dies. The electronic circuitry can include one or more integrated circuits (IC), such as application specific integrated circuits (ASICs). In some embodiments, one or more of the ICs can comprise a microbeamformer (μBF). In other embodiments, one or more of the ICs comprises a multiplexer circuit (MUX).

FIG. 2 is a diagrammatic top view of a portion of a scanner assembly 110, according to aspects of the present disclosure. The scanner assembly 110 includes a transducer array 124 formed in a transducer region 204 and transducer control logic dies 206 (including dies 206A and 206B) formed in a control region 208, with a transition region 210 disposed therebetween.

The transducer control logic dies 206 are mounted on a flexible substrate 214 into which the transducers 212 have been previously integrated. The flexible substrate 214 is shown in a flat configuration in FIG. 2. Though six control logic dies 206 are shown in FIG. 2, any number of control logic dies 206 may be used. For example, one, two, three, four, five, six, seven, eight, nine, ten, or more control logic dies 206 may be used.

The flexible substrate 214, on which the transducer control logic dies 206 and the transducers 212 are mounted, provides structural support and interconnects for electrical coupling. The flexible substrate 214 may be constructed to include a film layer of a flexible polyimide material such as KAPTON' (trademark of DuPont). Other suitable materials include polyester films, polyimide films, polyethylene napthalate films, or polyetherimide films, liquid crystal polymer, other flexible printed semiconductor substrates as well as products such as Upilex® (registered trademark of Ube Industries) and TEFLON® (registered trademark of E.I. du Pont). In the flat configuration illustrated in FIG. 2, the flexible substrate 214 has a generally rectangular shape. As shown and described herein, the flexible substrate 214 is configured to be wrapped around a support member 230 (FIG. 3) in some instances. Therefore, the thickness of the film layer of the flexible substrate 214 is generally related to the degree of curvature in the final assembled scanner assembly 110. In some embodiments, the film layer is between 5 μm and 100 μm, with some particular embodiments being between 5 μm and 25.1 μm, e.g., 6 μm.

The transducer control logic dies 206 is a non-limiting example of a control circuit. The transducer region 204 is disposed at a distal portion 221 of the flexible substrate 214. The control region 208 is disposed at a proximal portion 222 of the flexible substrate 214. The transition region 210 is disposed between the control region 208 and the transducer region 204. Dimensions of the transducer region 204, the control region 208, and the transition region 210 (e.g., lengths 225, 227, 229) can vary in different embodiments. In some embodiments, the lengths 225, 227, 229 can be substantially similar or, the length 227 of the transition region 210 may be less than lengths 225 and 229, the length 227 of the transition region 210 can be greater than lengths 225, 229 of the transducer region and controller region, respectively.

The control logic dies 206 are not necessarily homogenous. In some embodiments, a single controller is designated a master control logic die 206A and contains the communication interface for cable 112 which may serve as an electrical conductor, e.g., electrical conductor 218, between a processing system, e.g., processing system 106, and the scanner assembly 110. Accordingly, the master control circuit may include control logic that decodes control signals received over the cable 112, transmits control responses over the cable 112, amplifies echo signals, and/or transmits the echo signals over the cable 112. The remaining controllers are slave controllers 206B. The slave controllers 206B may include control logic that drives a transducer 212 to emit an ultrasonic signal and selects a transducer 212 to receive an echo. In the depicted embodiment, the master controller 206A does not directly control any transducers 212. In other embodiments, the master controller 206A drives the same number of transducers 212 as the slave controllers 206B or drives a reduced set of transducers 212 as compared to the slave controllers 206B. In an exemplary embodiment, a single master controller 206A and eight slave controllers 206B are provided with eight transducers assigned to each slave controller 206B.

To electrically interconnect the control logic dies 206 and the transducers 212, in an embodiment, the flexible substrate 214 includes conductive traces 216 formed in the film layer that carry signals between the control logic dies 206 and the transducers 212. In particular, the conductive traces 216 providing communication between the control logic dies 206 and the transducers 212 extend along the flexible substrate 214 within the transition region 210. In some instances, the conductive traces 216 can also facilitate electrical communication between the master controller 206A and the slave controllers 206B. The conductive traces 216 can also provide a set of conductive pads that contact the conductors 218 of cable 112 when the conductors 218 of the cable 112 are mechanically and electrically coupled to the flexible substrate 214. Suitable materials for the conductive traces 216 include copper, gold, aluminum, silver, tantalum, nickel, and tin, and may be deposited on the flexible substrate 214 by processes such as sputtering, plating, and etching. In an embodiment, the flexible substrate 214 includes a chromium adhesion layer. The width and thickness of the conductive traces 216 are selected to provide proper conductivity and resilience when the flexible substrate 214 is rolled. In that regard, an exemplary range for the thickness of a conductive trace 216 and/or conductive pad is between 1-5 μm. For example, in an embodiment, 5 μm conductive traces 216 are separated by 5 μm of space. The width of a conductive trace 216 on the flexible substrate may be further determined by the width of the conductor 218 to be coupled to the trace/pad.

The flexible substrate 214 can include a conductor interface 220 in some embodiments. The conductor interface 220 can be a location of the flexible substrate 214 where the conductors 218 of the cable 112 are coupled to the flexible substrate 214. For example, the bare conductors of the cable 112 are electrically coupled to the flexible substrate 214 at the conductor interface 220. The conductor interface 220 can be tab extending from the main body of flexible substrate 214. In that regard, the main body of the flexible substrate 214 can refer collectively to the transducer region 204, controller region 208, and the transition region 210. In the illustrated embodiment, the conductor interface 220 extends from the proximal portion 222 of the flexible substrate 214. In other embodiments, the conductor interface 220 is positioned at other parts of the flexible substrate 214, such as the distal portion 221, or the flexible substrate 214 may lack the conductor interface 220. A value of a dimension of the tab or conductor interface 220, such as a width 224, can be less than the value of a dimension of the main body of the flexible substrate 214, such as a width 226. In some embodiments, the substrate forming the conductor interface 220 is made of the same material(s) and/or is similarly flexible as the flexible substrate 214. In other embodiments, the conductor interface 220 is made of different materials and/or is comparatively more rigid than the flexible substrate 214. For example, the conductor interface 220 can be made of a plastic, thermoplastic, polymer, hard polymer, etc., including polyoxymethylene (e.g., DELRIN®), polyether ether ketone (PEEK™), nylon, Liquid Crystal Polymer (LCP), and/or other suitable materials.

Figure 3:
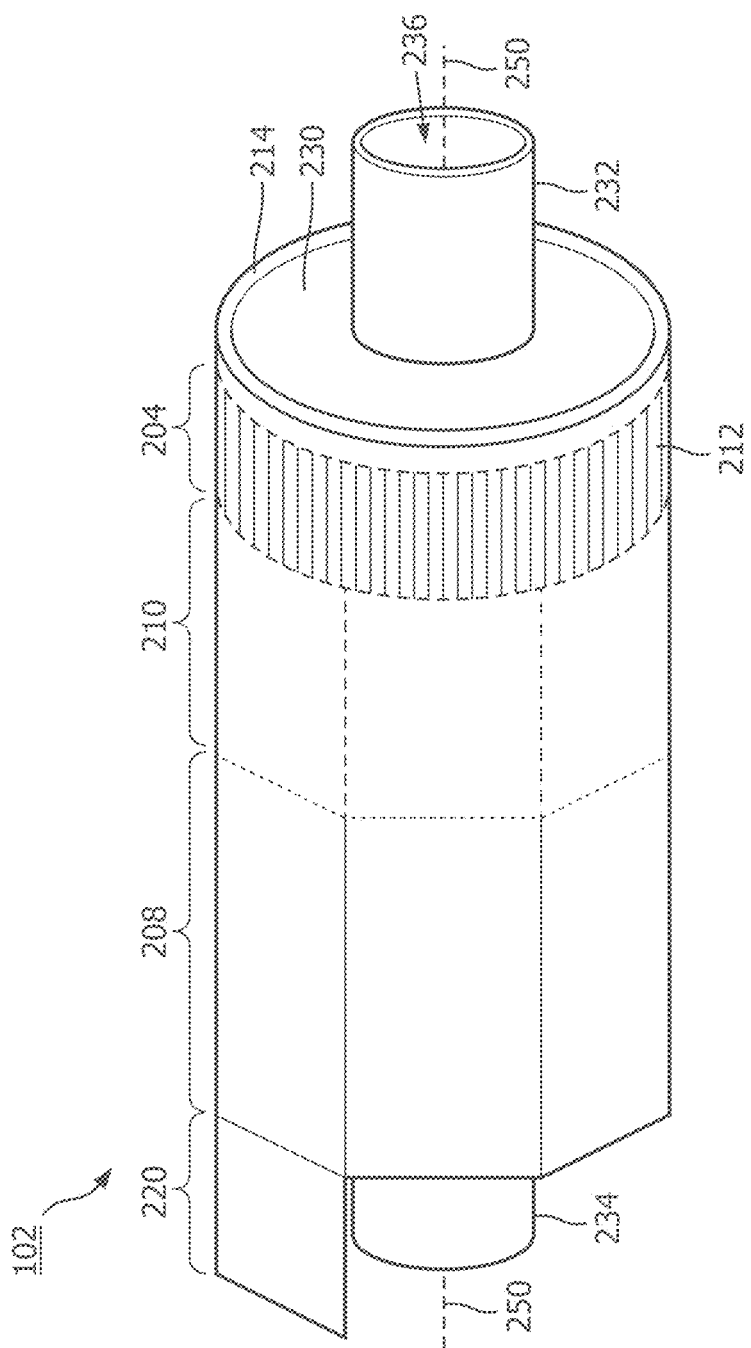
FIG. 3 is a diagrammatic perspective view of the scanner assembly shown in FIG. 2 in a rolled configuration around a support member, according to aspects of the present disclosure.

FIG. 3 illustrates a perspective view of the device 102 with the scanner assembly 110 in a rolled configuration. In some instances, the scanner assembly 110 is transitioned from a flat configuration (FIG. 2) to a rolled or more cylindrical configuration (FIG. 3). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND SENSING ASSEMBLY HAVING A FLEXIBLE SUBSTRATE," each of which is hereby incorporated by reference in its entirety.

In some embodiments, the transducer elements 212 and/or the controllers 206 can be positioned in in an annular configuration, such as a circular configuration or in a polygon configuration, around a longitudinal axis 250 of a support member 230. It will be understood that the longitudinal axis 250 of the support member 230 may also be referred to as the longitudinal axis of the scanner assembly 110, the flexible elongate member 121, and/or the device 102. For example, a cross-sectional profile of the scanner assembly 110 at the transducer elements 212 and/or the controllers 206 can be a circle or a polygon. Any suitable annular polygon shape can be implemented, such as a based on the number of controllers/transducers, flexibility of the controllers/transducers, etc., including a pentagon, hexagon, heptagon, octagon, nonagon, decagon, etc. In some examples, the plurality of transducer controllers 206 may be used for controlling the plurality of ultrasound transducer elements 212 to obtain imaging data associated with the vessel 120.

The support member 230 can be referenced as a unibody in some instances. The support member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, ('220 application) the entirety of which is hereby incorporated by reference herein. The support member 230 can be a ferrule having a distal flange or portion 232 and a proximal flange or portion 234. The support member 230 can be tubular in shape and define a lumen 236 extending longitudinally therethrough. The lumen 236 can be sized and shaped to receive the guide wire 118. The support member 230 can be manufactured using any suitable process. For example, the support member 230 can be machined and/or electrochemically machined or laser milled, such as by removing material from a blank to shape the support member 230, or molded, such as by an injection molding process.

Figure 4:
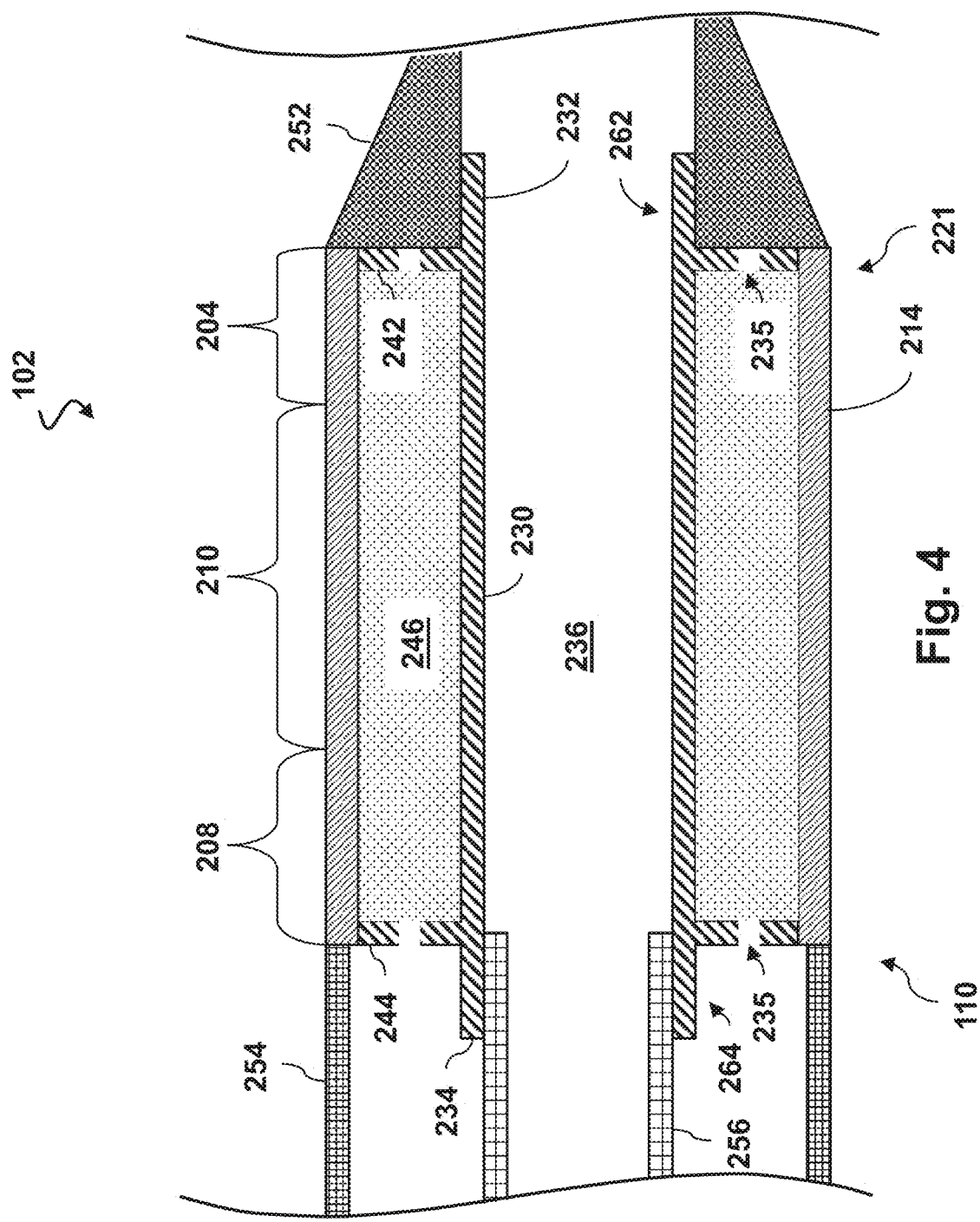
FIG. 4 is a diagrammatic cross-sectional side view of a scanner assembly in a rolled configuration around a support member, according to aspects of the present disclosure.

Referring now to FIG. 4, shown there is a diagrammatic cross-sectional side view of a distal portion of the intraluminal imaging device 102, including the flexible substrate 214 and the support member 230, according to aspects of the present disclosure. The support member 230 can be referenced as a unibody in some instances. The support member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, the entirety of which is hereby incorporated by reference herein. The support member 230 can be ferrule having a distal portion 262 and a proximal portion 264. The support member 230 can define a lumen 236 extending along the longitudinal axis LA. The lumen 236 is in communication with the entry/exit port 116 and is sized and shaped to receive the guide wire 118 (FIG. 1). The support member 230 can be manufactured according to any suitable process. For example, the support member 230 can be machined and/or electrochemically machined or laser milled, such as by removing material from a blank to shape the support member 230, or molded, such as by an injection molding process. In some embodiments, the support member 230 may be integrally formed as a unitary structure, while in other embodiments the support member 230 may be formed of different components, such as a ferrule and stands 242, 244, that are fixedly coupled to one another. In some cases, the support member 230 and/or one or more components thereof may be completely integrated with inner member 256. In some cases, the inner member 256 and the support member 230 may be joined as one, e.g., in the case of a polymer support member.

Stands 242, 244 that extend vertically are provided at the distal and proximal portions 262, 264, respectively, of the support member 230. The stands 242, 244 elevate and support the distal and proximal portions of the flexible substrate 214. In that regard, portions of the flexible substrate 214, such as the transducer portion 204 (or transducer region 204), can be spaced from a central body portion of the support member 230 extending between the stands 242, 244. The stands 242, 244 can have the same outer diameter or different outer diameters. For example, the distal stand 242 can have a larger or smaller outer diameter than the proximal stand 244 and can also have special features for rotational alignment as well as control chip placement and connection. To improve acoustic performance, any cavities between the flexible substrate 214 and the surface of the support member 230 are filled with a backing material 246. The liquid backing material 246 can be introduced between the flexible substrate 214 and the support member 230 via passageways 235 in the stands 242, 244. In some embodiments, suction can be applied via the passageways 235 of one of the stands 242, 244, while the liquid backing material 246 is fed between the flexible substrate 214 and the support member 230 via the passageways 235 of the other of the stands 242, 244. The backing material can be cured to allow it to solidify and set. In various embodiments, the support member 230 includes more than two stands 242, 244, only one of the stands 242, 244, or neither of the stands. In that regard the support member 230 can have an increased diameter distal portion 262 and/or increased diameter proximal portion 264 that is sized and shaped to elevate and support the distal and/or proximal portions of the flexible substrate 214.

The support member 230 can be substantially cylindrical in some embodiments. Other shapes of the support member 230 are also contemplated including geometrical, non-geometrical, symmetrical, non-symmetrical, cross-sectional profiles. As the term is used herein, the shape of the support member 230 may reference a cross-sectional profile of the support member 230. Different portions the support member 230 can be variously shaped in other embodiments. For example, the proximal portion 264 can have a larger outer diameter than the outer diameters of the distal portion 262 or a central portion extending between the distal and proximal portions 262, 264. In some embodiments, an inner diameter of the support member 230 (e.g., the diameter of the lumen 236) can correspondingly increase or decrease as the outer diameter changes. In other embodiments, the inner diameter of the support member 230 remains the same despite variations in the outer diameter.

A proximal inner member 256 and a proximal outer member 254 are coupled to the proximal portion 264 of the support member 230. The proximal inner member 256 and/or the proximal outer member 254 can comprise a flexible elongate member. The proximal inner member 256 can be received within a proximal flange 234. The proximal outer member 254 abuts and is in contact with the flexible substrate 214. A distal member 252 is coupled to the distal portion 262 of the support member 230. For example, the distal member 252 is positioned around the distal flange 232. The distal member 252 can abut and be in contact with the flexible substrate 214 and the stand 242. The distal member 252 can be the distal-most component of the intraluminal imaging device 102.

One or more adhesives can be disposed between various components at the distal portion of the intraluminal imaging device 102. For example, one or more of the flexible substrate 214, the support member 230, the distal member 252, the proximal inner member 256, and/or the proximal outer member 254 can be coupled to one another via an adhesive.

Figure 5:
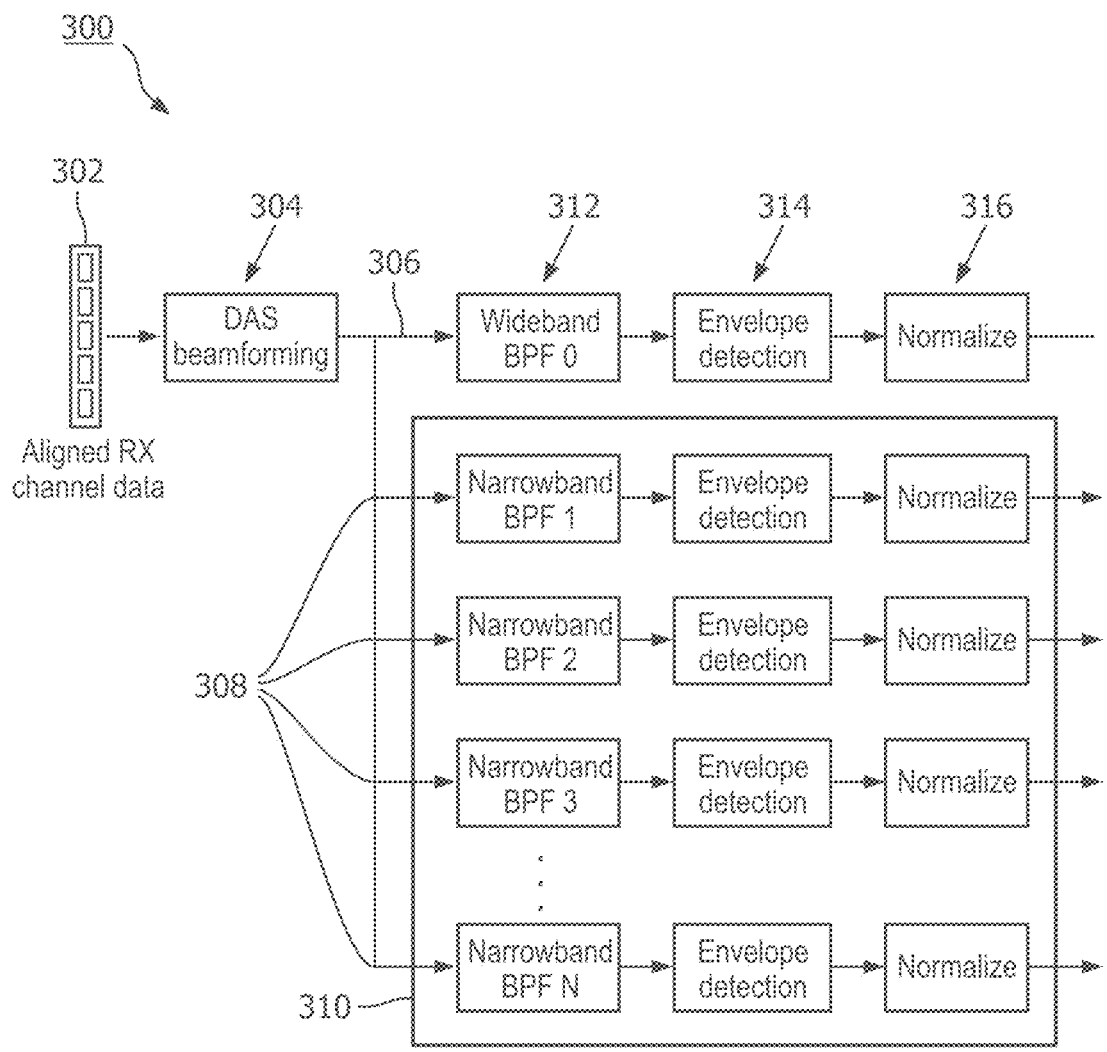
FIG. 5 is a flow diagram of a signal processing scheme for generating a grating-lobe-minimized image, according to aspects of the present disclosure.
Figure 5:
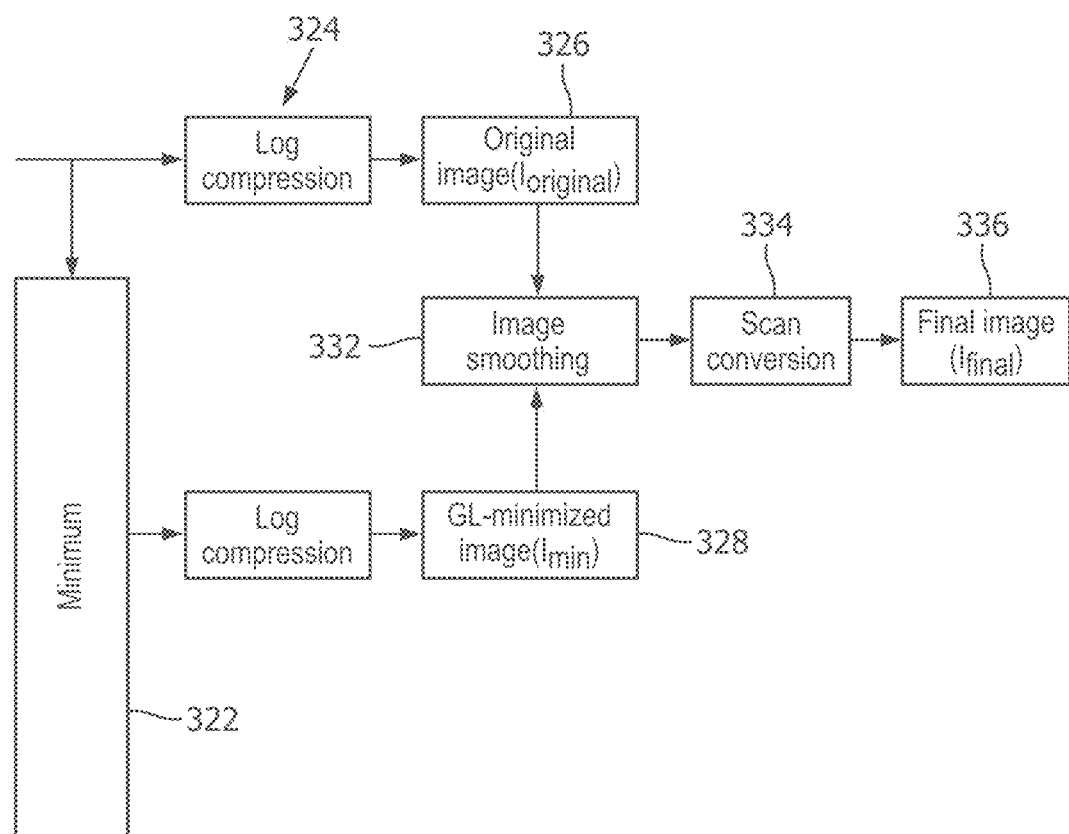

FIG. 5 is a flow diagram of a signal processing scheme 300 for generating a grating-lobe-minimized ultrasound image, according to some embodiments of the present disclosure. It will be understood that one or more steps of the process 300 shown in FIG. 5 can be carried out by an ultrasound imaging device and a processor or processing system, such as the IVUS imaging device 102 and processing system 106 illustrated in FIG. 1. In some embodiments, one or more steps of the process 300 can be divided and carried out by a plurality of processors in communication with one another. The ultrasound data obtained by the transducer array comprises one or more electrical signals representative of the echoes corresponding to the emitted ultrasound energy. One or more of steps described with respect to the FIG. 5 are applied to the electrical signal(s). In step 302 of the process 300 of FIG. 5, a beamformer receives aligned ultrasound data obtained by an ultrasound probe that includes an array of acoustic elements. The alignment of the ultrasound data can include, for example, applying delays to ultrasound signals received by the array of acoustic elements in order to focus the received signals. In step 304, the beamformer beamforms the received aligned ultrasound data by, for example, summing the aligned ultrasound data.

The processor duplicates and/or splits the beamformed ultrasound data into multiple processing paths, which can each comprise a duplicate ultrasound data set corresponding to the received ultrasound data. The processing paths include an original, or baseline path 306, and a plurality of narrowband paths 308. For the original, or baseline processing path 306, step 312 includes applying a wide band-pass filter to the beamformed ultrasound data. A band-pass filter is centered at a center frequency and comprises a bandwidth, or range of frequencies around the center frequency. The band-pass filter can be centered a center frequency of the acoustic elements of the ultrasound transducer array. In that regard, the ultrasound energy emitted by the acoustic elements and the echoes reflected from anatomy and received by the acoustic elements can be described in terms of their frequency. The electrical signal(s) representative of the ultrasound data, generated by the transducer array and processed by the processor, can also be described in terms of frequencies. The ultrasound energy emitted by the acoustic elements includes a range of frequencies, centered at the center frequency. The center frequency of the acoustic elements can be 2.5 MHz, 10 MHz, 20 MHz, 30 MHz, 40 MHz, 45 MHz, 60 MHz, 80 MHz, and/or other suitable values both larger and smaller. In some instances, the center frequency of the acoustic elements is fixed at manufacturing, while in other instances the center frequency of the acoustic elements can be variable, modified, selected, and/or controlled during use. The center frequency of the acoustic elements can depend on the imaging system. For example, the center frequency of the acoustic elements in an external ultrasound imaging probe can be different from the center frequency of the acoustic elements in an intraluminal imaging catheter. The wide band-pass filter applied on the path 306 can include all or a portion of the range of frequencies of the ultrasound energy emitted by the acoustic elements. The bandwidth can be described in terms of frequency (Hz), or in terms of a percentage of the center frequency. When described in terms of percentage, the bandwidth can be referred to as a fractional bandwidth. In an exemplary embodiment, the wide band-pass filter has a center frequency of approximately 20 MHz, and has a bandwidth of approximately 10 MHz, or a 50% fractional bandwidth. In some aspects, the frequency ranges of the band-pass filters may be based on the physical characteristics of the acoustic elements of the transducer array. For example, the elements of the array may be configured to emit ultrasound energy within a frequency ranges similar to that of the wide band-pass filter. Thus, the frequency range of the wide band-pass filter may be representative of the physical and/or electronic configuration of the acoustic elements.

Although the relatively wide bandwidth of the ultrasound data in the original processing path beneficially includes both low frequency and high frequency image data, which can produce high axial resolution and various tissue structures, the spatially-undersampled array of acoustic elements may provide ultrasound images having significant grating lobe artifacts, as explained further below with respect to FIG. 7A.

Aside from the original processing path 306, the processor splits the beamformed ultrasound data into N narrowband processing paths 308. The N narrowband processing paths 308 are processed by a grating-lobe-minimizing module 310. The module 310 may comprise or utilize the same processor used to carry out the other steps of the process 300, or a different processor. In that regard, the module 310 may comprise computer instructions stored in a memory that are executable by the processor. In step 312, for each of the N narrowband processing paths, the module 310 applies a different narrow band-pass filter (BPF1, BPF2, BPF3, . . . BPFN), each of which may correspond to a different frequency range or band. The frequency ranges of the narrow band-pass filters can correspond to frequencies of the ultrasound energy emitted by the acoustic elements and/or reflected ultrasound echoes. In the embodiment of FIG. 5, each of the frequency ranges of the narrow band-pass filters falls within the frequency range of the wide band-pass filter applied in the original processing path 306, such that the wide band-pass filter encompasses all of the narrow band-pass filters. In other embodiments, one or more frequency ranges of the narrow band-pass filters falls outside the frequency range of the wide band-pass filter. In some embodiments, the frequency range collectively spanned by all of the narrow band-pass filters spans the entirety of the frequency range of the wide band-pass filter, such that each and every frequency within the wide band-pass filter is included in a frequency range of at least one narrow band-pass filter. In other embodiments, some frequencies falling within the frequency range of the wide band-pass filter are not included in any frequency range of the narrow band-pass filters. In other words, in some embodiments, there are gaps between frequency ranges of the one or more narrow band-pass filters.

In some aspects, each of the frequency ranges of the narrow band-pass filters falls within the frequency range of the ultrasound energy emitted by the acoustic elements of the transducer array. Each narrow band-pass filter applied to the narrowband processing paths 308 may comprise overlapping or non-overlapping ranges of frequencies, and each may be centered at a different center frequency. In an overlapping example, a first narrowband frequency range spans from 13 MHz to 15 MHz, with a center frequency of 14 MHz, and an overlapping second narrow band frequency range spans from 14 MHz to 16 MHz, with a center frequency of 15 MHz. In a non-overlapping example, the first narrowband frequency range spans from 13 MHz to 14.99 MHz, with a center frequency of 14 MHz, and the second narrowband frequency range spans from 16 MHz to 18 MHz, with a center frequency of 17 MHz.

In an exemplary embodiment, the wide band-pass filter is centered around 20 MHz with a bandwidth of approximately 10 MHz, or 50%. Each narrow band-pass filter has a center frequency somewhere between 13 MHz and 27 MHz, and has a bandwidth of approximately 20%. In another embodiment, the wide band-pass filter is centered around 2.5 MHz with a bandwidth of about 50%, and 5 different narrow band-pass filters are applied, each of which comprises a bandwidth of about 10%. In other embodiments, fewer or more band-pass filters can be applied, for example, 2, 3, 4, 6, 7, 10, 15, 20, or any other suitable number of band-pass filters. Different types of ultrasound transducer arrays can be configured to emit ultrasound energy at a different center frequency, and with a different bandwidth, or frequency range. For example, in some embodiments, an external ultrasound probe emits ultrasound energy at a center frequency of about 2.5 MHz, and with a fractional bandwidth of about 50%. By contrast, in some embodiments, an IVUS imaging catheter may emit ultrasound energy at a center frequency of about 20 MHz and a fractional bandwidth of about 50%.

In some embodiments, the center frequency and/or frequency range of the wide band-pass filter and/or the narrow band-pass filters can be higher or lower, depending on the configuration of the acoustic elements of the transducer array. For example, the frequency range or bandwidth can be approximately 5%, 10%, 15%, 20%, 25%, 30%, 40%, or any other suitable value. In other terms, the frequency range can be 1 MHz, 5 MHz, 7 MHz, 12 MHz, 15 MHz, 20 MHz, or any other suitable bandwidth. In some embodiments, the center frequency of the wide band-pass filter and/or the narrow band-pass filters can be 2 MHz, 5 MHz, 10 MHz, 15 MHz, 25 MHz, 30 MHz, 40 MHz, 45 MHz, 60 MHz, 80 MHz, or any other suitable frequency. In an exemplary embodiment, each of the frequency ranges of the narrowband filters is narrower than the first frequency range of the wide band-pass filter.

The various narrow band-pass filters can affect the location or appearance of grating lobe artifacts in the ultrasound image. This is because the grating lobe location is determined by the following relationship:

$$\theta_g = \pm \sin^{-1} \frac{\lambda}{d}$$

where $\theta_g$ is the angle at which the grating lobe occurs, $\lambda$ is the wavelength, and d is the pitch of the image array. Since the pitch d is fixed, the grating lobe angle $\theta_g$ changes as a function of the wavelength $\lambda$. Embodiments of the present disclosure use band-pass filters at different frequencies (and therefore different wavelengths) to generate images with grating lobes at different locations. The variance of the location of the grating lobe artifacts can be advantageously used to reduce the appearance of the grating lobes in ultrasound images, as explained further below.

In steps 314 and 316, the system uses envelope detection by, for example, applying a Hilbert transformation to the filtered ultrasound data, and normalizes the filtered data for each of the processing paths 306, 308 to create a plurality of filtered images. In some embodiments, normalizing the filtered data can include taking into account an energy level in each frequency band. This can be beneficial, as the transducer frequency band is typically a bell-shaped curve, and thus, lower and higher frequency bands will have lower energy than the center portion of the transducer band. In some aspects, the plurality of filtered images can be referred to as duplicate images although their individual image content may vary based on the different band-pass filters applied. In step 322, the processor generates a grating-lobe-minimized (GL-minimized) 328 image by computing a pixel-by-pixel minimum from among the N different narrowband images. Computation of the pixel-by-pixel minimum is explained in FIG. 6.

Figure 6:
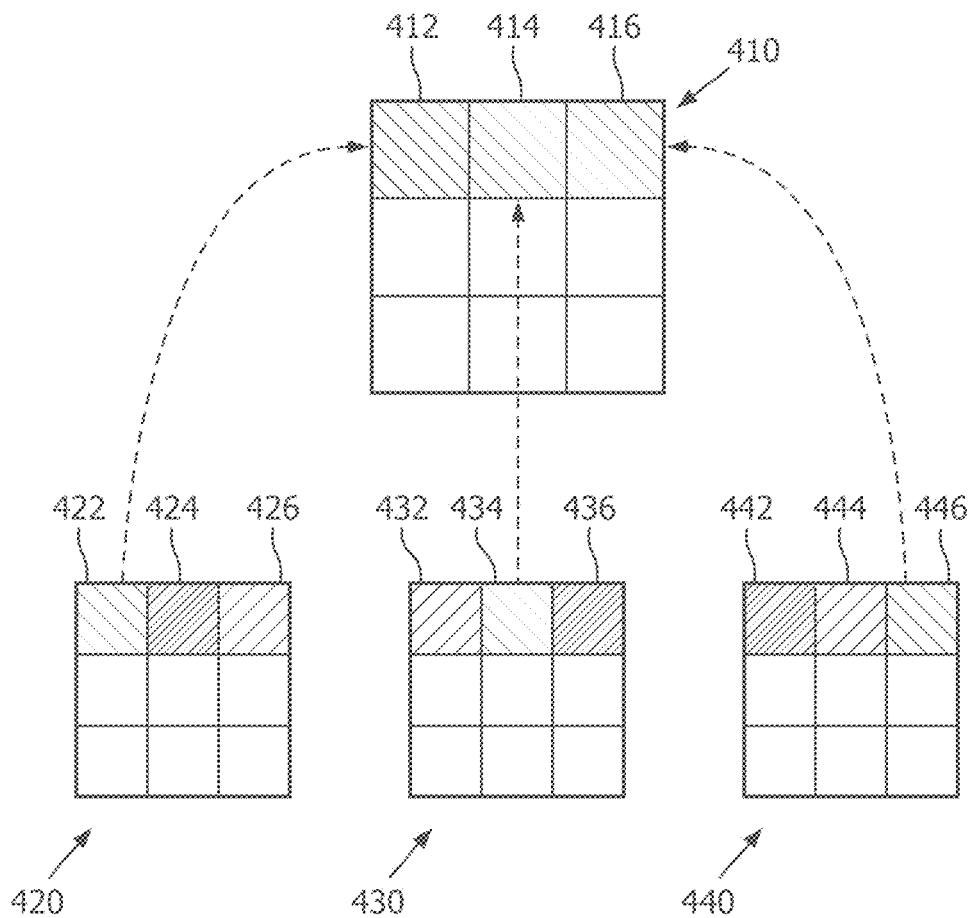
FIG. 6 is a diagrammatic graphical view of a process for generating a grating-lobe-minimized image from a plurality of narrow-band images, according to aspects of the present disclosure.

FIG. 6 shows three images 420, 430, 440, each comprising a matrix of nine pixels. Each of the images 420, 430, 440 is at least slightly different from the others, which may be the result of different band-pass filters applied to the ultrasound data to generate each image. In some embodiments, one of the images is an original image generated using a wide band-pass filter, and the other images are narrowband images generated using a plurality of different narrow band-pass filters. For simplicity of explanation, each of the images 420, 430, and 440 shown in FIG. 6 is a narrowband image. The intensity of each pixel (e.g., 422, 432, 442) of the narrowband images is representative of the strength of the received ultrasound signal, or echo, corresponding to a location in a field of view. In that regard, because the narrowband images 420, 430, and 440 are all representative of a same field of view, the individual pixels of each image 420, 430, 440 spatially correspond to one another. Different strengths or intensities of the received signals are illustrated in FIG. 6 as different patterns and shades, where lighter patterns correspond to relatively weaker signals or echoes.

A composite GL-minimized image 410 is formed by selecting from among the narrowband images 420, 430, 440 the minimum strength or minimum signal corresponding to each pixel. In that regard, pixel 422 from the first narrowband image 420 is selected as pixel 412 for the GL-minimized image, as it comprises the lowest (i.e. minimum) signal strength, or intensity, shown by its relatively lighter pattern when compared to corresponding pixels 432 and 442 of the second narrowband image 430 and third narrowband image 440. Similarly, pixel 434 is selected as pixel 414 for the GL-minimized image 410, and pixel 446 is selected as pixel 416 for the GL-minimized image 410. Pixels 432, 436, 442, and 444 are ignored or discarded. It will be understood that although FIG. 6 illustrates each of the minimum selected pixels 412, 414, and 416 as having the same shade or intensity, the minimum signal values selected in step 322 need not be equal. In many instances, the intensity or strength of each of the selected minimum signals will vary. For example, in some aspects, the GL-minimized image 410 generated in step 322 of the process 300 will comprise pixels of a plurality of different signal strengths or shades, both lighter and darker.

The varying pattern of pixel intensity in the GL-minimized images 420, 430, and 440, may be the result of the different narrow band-pass filters applied to the ultrasound data, which, as described above, results in a different grating lobe angle or location. For example, pixel 424 may be representative of a grating lobe artifact in the first narrowband image 420. By applying a different band-pass filter to produce the second narrowband image 430, the relative location of the grating lobe artifact changes, and moves to pixel 436 in the second narrowband image 430, which spatially corresponds to pixel 426.

Referring again to FIG. 5, in step 324 the GL-minimized ultrasound image 328 generated in processing paths 308 by in the GL-minimizing module 310, and the original or baseline ultrasound image 326 generated by the first processing path 306 each undergo a separate log compression. The log compressions performed can be the same type of log compression or different log compressions. The effects of the GL-minimizing module 310 can be shown with respect to FIGS. 7A-C, which are exemplary views of IVUS images of a stent.

Figure 7A:
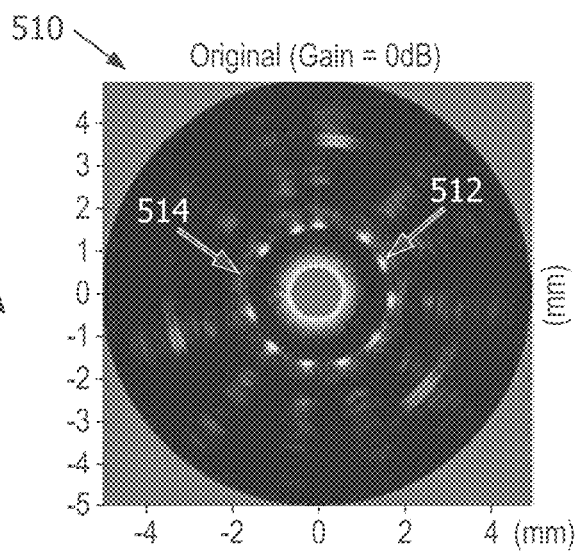
FIG. 7A is an exemplary view of an intravascular ultrasound (IVUS) image, according to aspects of the present disclosure.

FIG. 7A depicts an original ultrasound image 510 that shows a plurality of stent struts 512 and has been processed along the first processing path, without the GL-minimizing module 310. The original ultrasound image 510 shown in FIG. 7A was generated by applying a wide band-pass filter to the ultrasound data. The stent struts 512 can be seen as bright spots in a circular pattern around the center of the image 510. Grating lobe artifacts 514 of the stent struts 512 are seen between and around the stent struts 512 as blurry, off-axis objects. As explained above, these grating lobe artifacts 514 can complicate the diagnosis and analysis process, especially for less-experienced technicians.

Figure 7B:
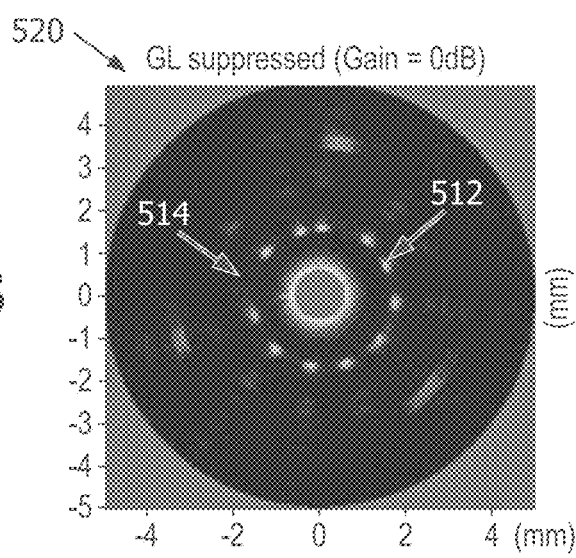
FIG. 7B is an exemplary view of a grating-lobe-minimized IVUS image, according to aspects of the present disclosure.
Figure 7C:
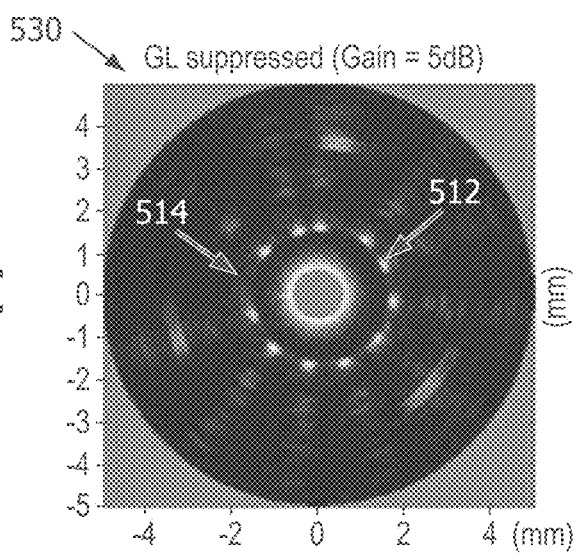
FIG. 7C is an exemplary view of a grating-lobe-minimized IVUS image with an increased gain, according to aspects of the present disclosure.

FIG. 7B depicts the GL-minimized image 520 generated by the GL-minimizing module 310 described above. The stent struts 512 appear again as bright spots in the same locations. However, the grating lobe artifacts 514 that appeared in FIG. 7A are significantly reduced in FIG. 7B. Additionally, the stent struts 512 appear slightly dimmed in FIG. 7B as a result of the GL-minimizing process. In order to increase the contrast and/or visibility of desirable image features, such as the stent struts 512, the gain of the GL-minimized image 520 is increased in the image 530 FIG. 7C to increase the brightness of the desirable image features. Although increasing the gain may also slightly increase the brightness of any residual grating lobe artifacts 514, the grating lobe artifacts 514 shown in FIG. 7C are significantly reduced notwithstanding the increase in gain.

Referring again to FIG. 5, while GL-minimized images can have reduced grating lobe artifacts, the speckle texture representative of tissue can also be adversely affected or reduced by the pixel-by-pixel minimizing operation, which can result in a blocky image appearance. Thus, in order to retain desirable speckle texture, the original image 326 and GL-minimized image 328 are combined and smoothed in step 332. In some embodiments, combining the images is performed according to the relationship:

$I_{final} = L_{min} + H_{original}$, where $L_{min} = LPF(I_{min})$, $H_{original} = I_{original} - LPF(I_{original})$, and LPF=spatial low-pass filter In other words, $L_{min}$ can be described as a smoothed version (or, spatially low-pass filtered version) of the GL-minimized image ($I_{min}$) 328. $L_{min}$ may show the more salient or reflective elements in the field of view, such as stent struts, while minimizing grating lobe artifacts, and, as explained above, reduced speckle texture. By contrast, $H_{original}$ can be described as the high spatial frequency component of the original image 326.

Figure 8A:
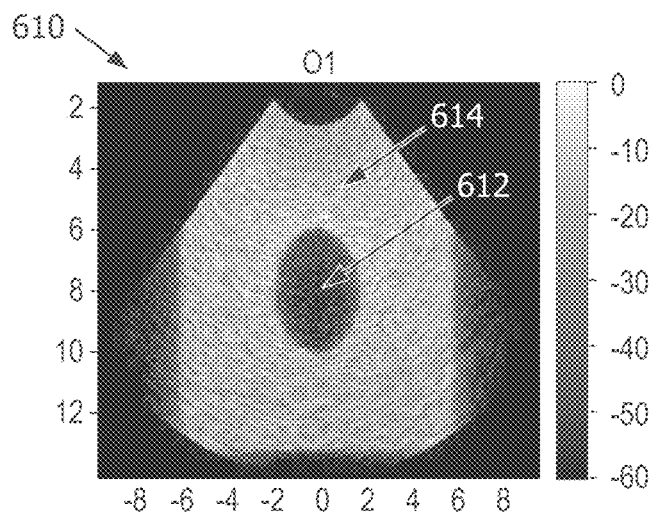
FIG. 8A is an exemplary view of an ultrasound image obtained by an external ultrasound probe, according to aspects of the present disclosure.
Figure 8B:
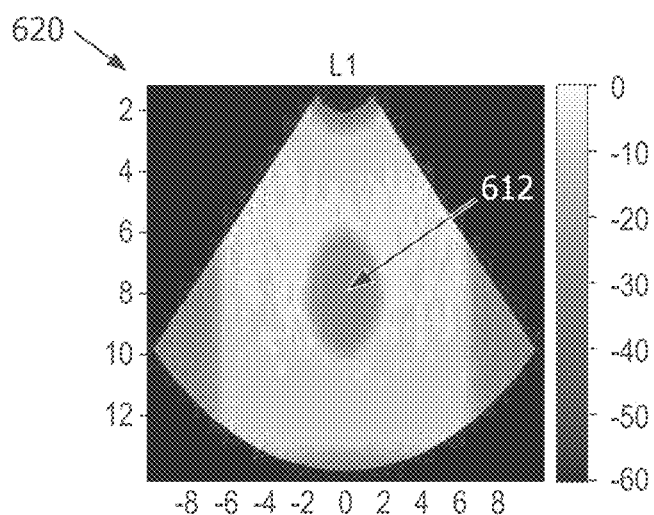
FIG. 8B is an exemplary view of a spatially-low-pass-filtered ultrasound image generated from the ultrasound image shown in FIG. 8A, according to aspects of the present disclosure.
Figure 8C:
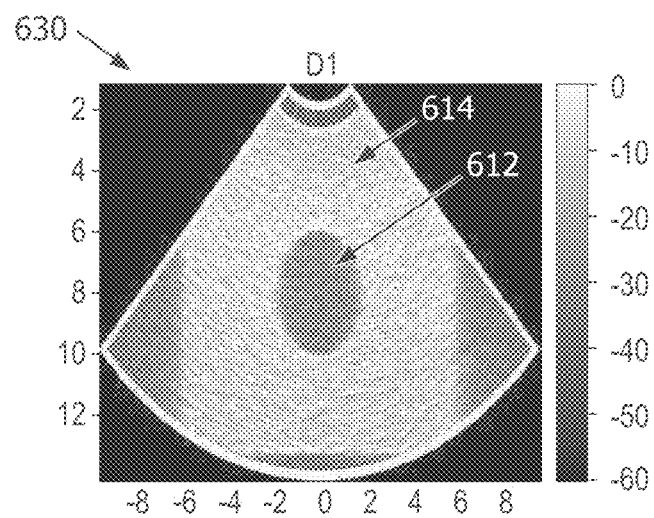
FIG. 8C is an exemplary view of high spatial frequency ultrasound image generated based on the ultrasound image of FIG. 8A and the spatially-low-pass-filtered ultrasound image shown in FIG. 8B, according to aspects of the present disclosure.

FIGS. 8A-C depict an original, non-GL-minimized image ($I_{original}$), a low-pass filtered original image ($LPF(I_{original})$), and a high spatial frequency image ($H_{original}$), respectively. It will be understood that the B-mode images 610, 620, and 630 shown in FIGS. 8A-C are obtained by an external ultrasound probe, rather than an IVUS imaging catheter, as the images shown in FIGS. 7A-C. In that regard, the systems and methods for minimizing grating lobe artifacts described in the present disclosure are applicable to any ultrasound probe, catheter, or device that uses an array of acoustic elements to generate an image. For example, the signal processing techniques described herein can be used for IVUS imaging, as shown in FIGS. 7A-C, external ultrasound imaging, intracardiac echocardiography (ICE), transesophageal echocardiography (TEE), or any other suitable ultrasound imaging modality.

FIG. 8A is an original B-mode ultrasound image 610 ($I_{original}$), which is formed using a wide band-pass filter, and includes high contrast features, such as the dark shape 612 near the center of the image, and high spatial frequency data, such as the speckle texture 614. The image 620 of FIG. 8B is a spatially-low-pass-filtered version of the original image 610 shown in FIG. 8A. The low-pass filter applied in FIG. 8B may be the same or low-pass filter applied in FIG. 8A, or a different low-pass filter. The spatial low pass filtering reduces the speckle texture 614 in the image 620, and forms a blurred image that isolates the larger high-contrast object information in the image 620, including the dark shape 612. FIG. 8C is a high spatial frequency image 630 formed by subtracting the spatially-low-pass filtered image 620 from the original image 610 to isolate the high spatial frequency components of the original image 610, such as the speckle texture 614. The high spatial frequency image 630 can be combined with a GL-minimized image to achieve the advantages of reduced grating lobe artifacts while not losing important image features and information contained in the high spatial frequency component of the original image 610.

Referring again to FIG. 5, in step 332, the original image 326 and GL-minimized image 328 are combined as described above, and smoothed. Smoothing can include applying a spatial low pass filter to the combined image. The combined and smoothed image then undergoes a scan conversion in step 334 to produce the final image ($I_{final}$). The final image is then output to a display in step 336.

Figure 9:
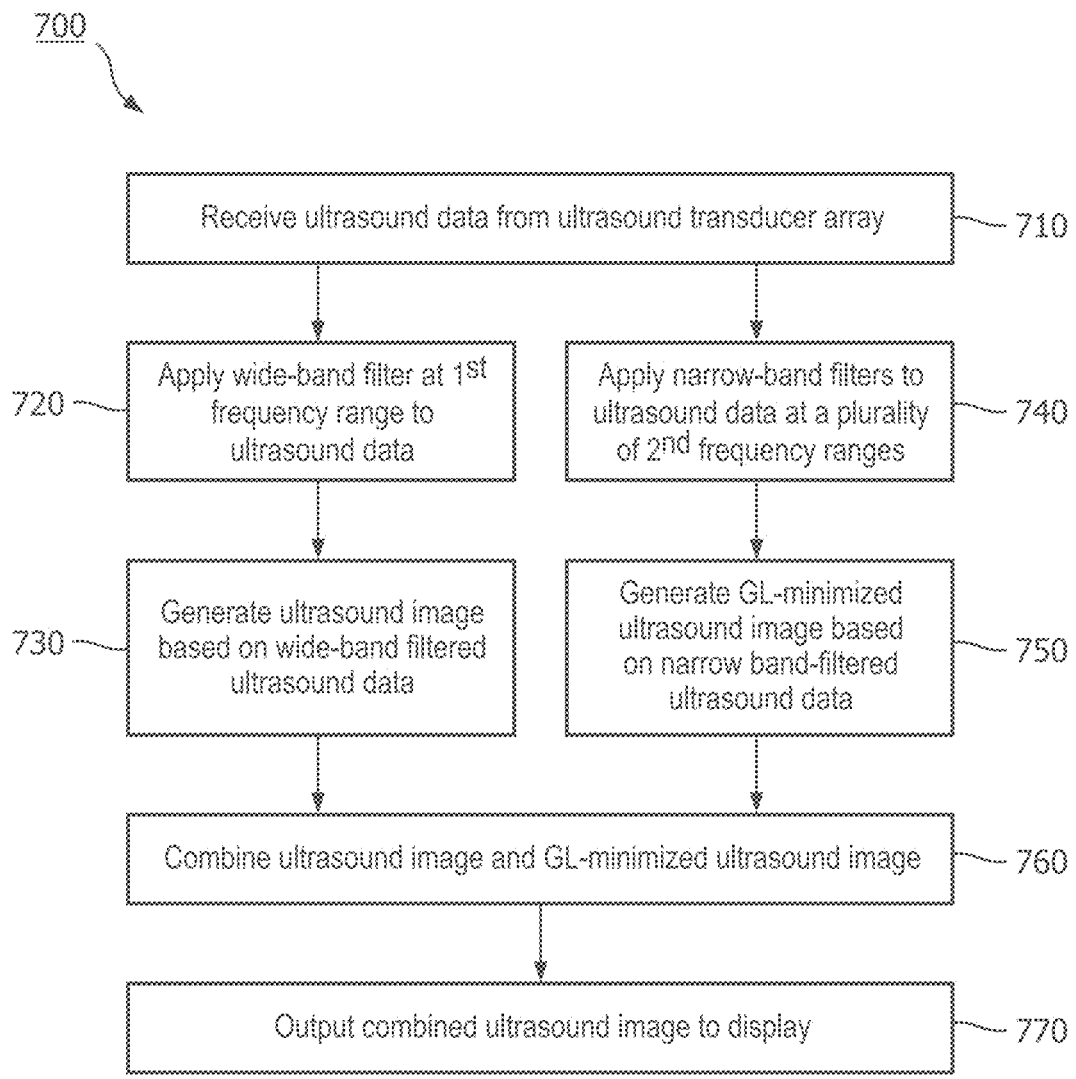
FIG. 9 is a flow diagram of a method for generating a grating-lobe-minimized ultrasound image, according to aspects of the present disclosure.
Figure 10:
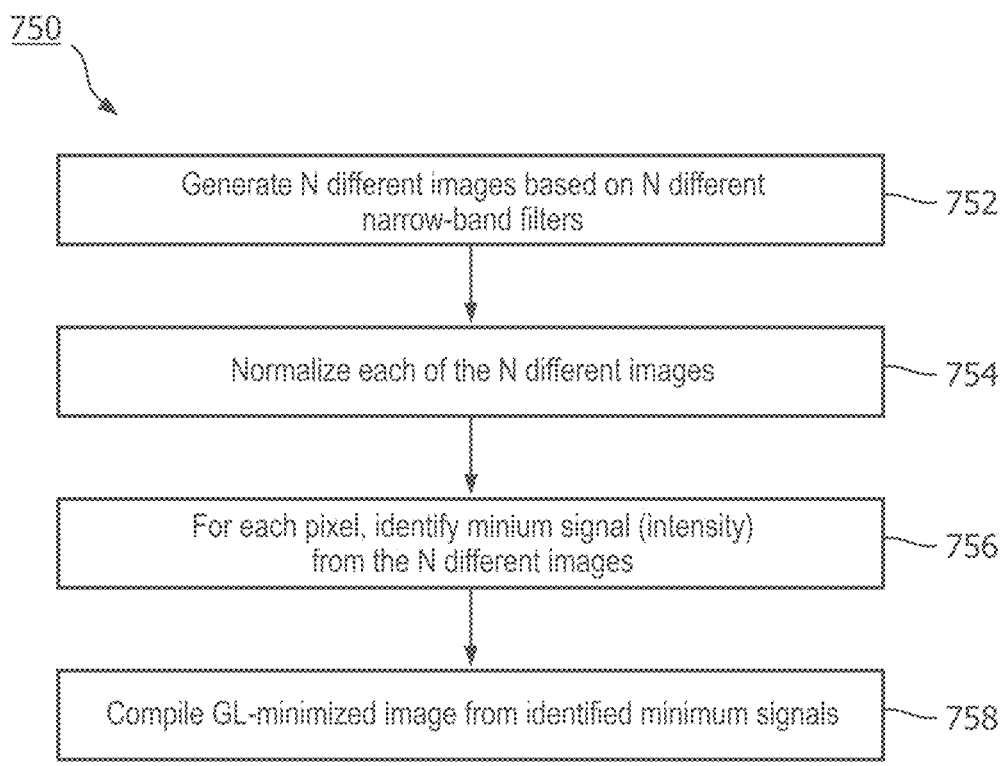
FIG. 10 is a flow diagram of a step of the method of FIG. 9, according to aspects of the present disclosure.
Figure 11:
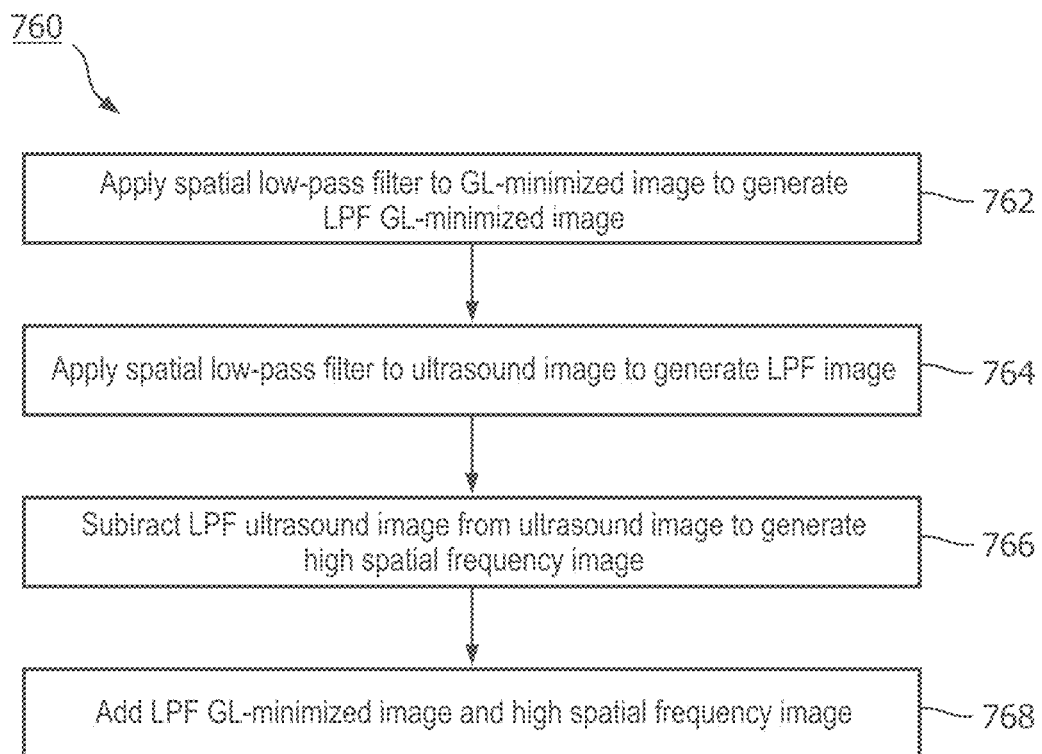
FIG. 11 is a flow diagram of a step of the method of FIG. 9, according to aspects of the present disclosure.

FIGS. 9-11 are flow diagrams illustrating a method for generating a GL-minimized image, according to some embodiments of the present disclosure. As shown in FIG. 9, a processor receives ultrasound data from an ultrasound transducer array in step 710. The transducer array is configured to emit ultrasound energy, receive echoes corresponding to the emitted ultrasound energy, and transmit ultrasound data or signals that are representative of the received echoes. In some embodiments, the array comprises a one-dimensional array, a 1.5-dimensional array, or a two-dimensional array of acoustic elements. The acoustic elements can comprise lead zirconate titanate (PZT) transducers, piezoelectric micromachined ultrasound transducers (PMUT), capacitive micromachined ultrasound transducers (CMUT), or any other suitable type of acoustic element. In some embodiments, the array is part of an IVUS imaging device, as described above with respect to FIGS. 1-4. In other embodiments, the array is part of an external imaging probe configured to non-invasively obtain images by pressing the array of the probe adjacent the patient's skin. In still other embodiments, the array is part of an ICE imaging probe, a TEE probe, or any other suitable type of ultrasound device that comprises an array of acoustic elements.

In step 720, a wide-band filter is applied to the received ultrasound data. The wide-band filter can be characterized by a first frequency range, which comprises a first bandwidth centered around a first frequency. In an exemplary embodiment, the wide-band filter is centered around 20 MHz with a bandwidth of approximately 10 MHz, or 50%. In other embodiments, the first frequency and/or first frequency range can be higher or lower. For example, the first frequency range or bandwidth can be approximately 1 MHz, 5 MHz, 7 MHz, 12 MHz, 15 MHz, 20 MHz, or any other suitable bandwidth. In some embodiments, the first frequency on which the bandwidth is centered can be 2 MHz, 5 MHz, 10 MHz, 15 MHz, 25 MHz, 30 MHz, 40 MHz, 45 MHz, 60 MHz, 80 MHz, or any other suitable frequency. In step 730, an ultrasound image, which may be referred to as an original or baseline image, is formed based on the broadband ultrasound data described with respect to step 720. Step 730 may include using envelope detection and normalization in order to generate the image.

In step 740, a plurality of narrow band-pass filters are applied to the ultrasound data at a second plurality of frequency ranges or frequency bands. In an exemplary embodiment, each of the frequency ranges of the narrow-band filters is narrower than the first frequency range of the wide band-pass filter applied in step 720. For example, each of the frequency ranges of the second plurality can fall within the first frequency range of the wide-band filter. In other embodiments, one or more of the second plurality of frequency ranges falls outside the first frequency range. In step 750, a GL-minimized ultrasound image is generated based on the narrow-band-filtered ultrasound data. An embodiment of step 750 is detailed in FIG. 10. In step 752, N different images are generated based on the N-different narrow-band filters applied in step 740. In one embodiment, 15 different narrow band-pass filters are used. The band-pass filters have center frequencies ranging from 13 MHz to 27 MHz, each having a 20% bandwidth. In another embodiment, the wide band-pass filter is centered around 2.5 MHz with a bandwidth of about 50%, and 21 different narrow band-pass filters are applied, each of which comprises a bandwidth of about 10%.

In step 754, each of the N different images is normalized. Normalizing can help to account for variations in signal strength among the N different images after the band-pass filters are applied. In some aspects, normalization can be based on an energy level for each frequency band, as discussed above. Because signal strength may depend, in part, on the center frequency and bandwidth of the of band-pass filters, the normalization in step 754 can account for these variations. In step 756, a pixel-by-pixel minimum calculation is performed, wherein each of the N different narrowband images is analyzed to identify and select a minimum signal corresponding to each pixel. In step 758, each of the minimum signals or pixels is combined to form the GL-minimized image.

Referring again to FIG. 9, in step 760, the ultrasound image and GL-minimized ultrasound image are combined to form a final ultrasound image. An embodiment of step 760 is detailed in FIG. 11. In step 762, a spatial low-pass filter is applied to generate an LPF GL-minimized ultrasound image. Spatial low-pass filtering may comprise an image convolution to reduce or eliminate the high spatial frequency component of an ultrasound image. In other words, spatial low-pass filtering can soften or blur the image. In step 764, a spatial low-pass filter is applied to the original ultrasound image to generate an LPF ultrasound image. In step 766, the LPF ultrasound image created in step 764 is subtracted from the original ultrasound image to generate a high spatial frequency image. As explained above, the high spatial frequency image may isolate the speckle texture of the original image, while reducing or excluding the larger high-contrast portions of the image. In step 768, the LPF GL-minimized image created in step 762 is added or combined with the high spatial frequency image created in step 766 to create the final image. Referring again to FIG. 9, in step 770, the final image is output to a display.

It will be understood that the method 700 described with respect to FIGS. 9-11 can be modified in a number of ways. For example, in some embodiments, a gain is applied in the image to make certain features in the image appear brighter or darker. For example, in one embodiment, a gain of 5 dB is applied. In other embodiments, more or less gain is applied, such as 1 dB, 2 dB, 4 dB, 6 dB, 8 dB, etc.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ultrasound imaging system, comprising:
a processor configured for communication with an ultrasound transducer array and a display, wherein the processor is configured to:
receive ultrasound data from the ultrasound transducer array;
generate, using the ultrasound data, a first ultrasound image based on a first frequency range of the ultrasound data;
generate, using the ultrasound data, a plurality of second ultrasound images respectively based on a plurality of second frequency ranges of the ultrasound data, wherein each of the plurality of second ultrasound images comprises a first pixel and a second pixel within a same field of view;
identify the first pixel in one of the plurality of second ultrasound images from among the first pixels of the plurality of second ultrasound images, based on the pixel intensity;
identify the second pixel in another of the plurality of second ultrasound images from among the second pixels of the plurality of second ultrasound images; and
use the first pixel from the one of the plurality of second ultrasound images and the second pixel from the another of the plurality of second ultrasound images to generate a grating-lobe-minimized ultrasound image;
combine the first ultrasound image and the grating-lobe-minimized ultrasound image to generate a combined ultrasound image; and
output the combined ultrasound image to the display,
wherein the first ultrasound image, the plurality of second ultrasound images, and the grating-lobe-minimized ultrasound image are representative of the same field of view,
wherein the grating-lobe-minimized ultrasound image comprises a third pixel and a fourth pixel within the same field of view,
wherein the third pixel is distinct from the fourth pixel,
wherein the third pixel comprises the first pixel from the one of the plurality of second ultrasound images and the fourth pixel comprises the second pixel from the another of the plurality of second ultrasound images.

2. The ultrasound imaging system of claim 1, further comprising the ultrasound transducer array.

3. The ultrasound imaging system of claim 2, further comprising an intravascular ultrasound (IVUS) imaging catheter, wherein the ultrasound transducer array is positioned around a circumference of the IVUS imaging catheter.

4. The ultrasound imaging system of claim 1, wherein the processor is configured to:
duplicate the ultrasound data to generate a plurality of duplicate ultrasound data sets; and
generate the plurality of second ultrasound images based on the plurality of duplicate ultrasound data sets.

5. The ultrasound imaging system of claim 1, wherein the processor is configured to:
normalize the plurality of second ultrasound images.

6. The ultrasound imaging system of claim 1, wherein the first pixel in each of the plurality of second ultrasound images is representative of a same first location in the same field of view and the second pixel in each of the plurality of second ultrasound images is representative of a same second location in the same field of view.

7. The ultrasound imaging system of claim 6,
wherein the processor is configured to identify the first pixel in the one of the plurality of second ultrasound images based on the pixel intensity being at a minimum for the same first location, and
wherein the processor is configured to identify the second pixel in the one of the plurality of second ultrasound images based on the pixel intensity being at a minimum for the same second location.

8. The ultrasound imaging system of claim 1, wherein the first frequency range is broader than each of the plurality of second frequency ranges.

9. The ultrasound imaging system of claim 1, wherein at least one of the plurality of second frequency ranges is outside of the first frequency range.

10. The ultrasound imaging system of claim 1,
wherein, to generate the first ultrasound image, the processor is configured to apply a wide band-pass filter with a first bandwidth to the ultrasound data, wherein the first bandwidth corresponds to the first frequency range,
wherein, to generate the plurality of second ultrasound images, the processor is configured to apply a plurality of narrow band-pass filters with respective second bandwidths to the ultrasound data, wherein the respective second bandwidths correspond to the plurality of second frequency ranges.

11. The ultrasound imaging system of claim 10, wherein the first bandwidth is different than the respective second bandwidths.

12. The ultrasound imaging system of claim 10, wherein the respective second bandwidths are different from one another.

13. The ultrasound imaging system of claim 1, wherein, to combine the first ultrasound image and the grating-lobe-minimized ultrasound image, the processor is configured to:
apply a first spatial low-pass filter (LPF) to the grating-lobe-minimized ultrasound image to generate an LPF grating-lobe-minimized ultrasound image;
apply a second spatial LPF to the first ultrasound image to generate an LPF ultrasound image;
subtract the LPF ultrasound image from the first ultrasound image to generate a high spatial frequency ultrasound image; and
add the LPF grating-lobe-minimized ultrasound image and the high spatial frequency ultrasound image.

* * * * *